US005639859A

United States Patent [19]
Kunz et al.

[11] Patent Number: 5,639,859
[45] Date of Patent: *Jun. 17, 1997

[54] CARBOXYLATE PROTECTIVE GROUPS, A PROCESS FOR THEIR PREPARATION, THEIR COUPLING TO A FUNCTIONAL GROUP, AND THEIR USE

[75] Inventors: Horst Kunz, Mainz; Günther Braum, Wiesbaden; Peter Braun, Mainz, all of Germany

[73] Assignee: Hoechst Aktiengesellschaft, Frankfurt am Main, Germany

[*] Notice: The term of this patent shall not extend beyond the expiration date of Pat. No. 5,439,806.

[21] Appl. No.: 440,836

[22] Filed: May 15, 1995

Related U.S. Application Data

[62] Division of Ser. No. 226,367, Apr. 12, 1994, Pat. No. 5,439,806, which is a continuation of Ser. No. 957,004, Oct. 6, 1992, abandoned.

[30] Foreign Application Priority Data

Oct. 7, 1991 [DE] Germany ............ 41 33 139.7
Apr. 25, 1992 [DE] Germany ............ 42 13 706.3

[51] Int. Cl.$^6$ ................ C07K 1/06; C07K 5/06
[52] U.S. Cl. ............. 530/337; 530/333; 560/204; 560/78; 435/68.1; 435/106
[58] Field of Search ............ 560/98, 204; 530/337, 530/333

[56] References Cited

U.S. PATENT DOCUMENTS

| | | | |
|---|---|---|---|
| 3,960,830 | 6/1976 | Bayer et al. | 260/112.5 R |
| 4,179,337 | 12/1979 | Davis et al. | 435/181 |
| 4,256,836 | 3/1981 | Isowa et al. | 435/70 |
| 4,339,534 | 7/1982 | Johansen et al. | 930/10 |
| 4,649,156 | 3/1987 | Tanaka et al. | 514/530 |
| 4,668,628 | 5/1987 | Dahod et al. | 435/135 |
| 4,841,091 | 6/1989 | Tanaka et al. | 560/121 |
| 4,963,492 | 10/1990 | Keller et al. | 435/280 |
| 5,037,751 | 8/1991 | Bertola et al. | 435/198 |
| 5,089,392 | 2/1992 | Miller et al. | 560/138 |
| 5,108,916 | 4/1992 | Cobbs et al. | 435/135 |
| 5,159,102 | 10/1992 | Tanaka et al. | 560/121 |
| 5,169,780 | 12/1992 | Stirling et al. | 435/280 |

FOREIGN PATENT DOCUMENTS

| | | |
|---|---|---|
| 35474/84 | 9/1988 | Australia. |
| 1278795 | 1/1991 | Canada. |
| 0145956 | 6/1985 | European Pat. Off.. |
| 0527427 | 2/1993 | European Pat. Off.. |
| 3528631 | 2/1987 | Germany. |
| 54-119260 | 9/1979 | Japan. |

OTHER PUBLICATIONS

Mutter et al. (1979). "The liquid–Phase Method for Peptide Synthesis," In Peptides, vol. 2, 179, Chapeter 2, pp. 286–332 1979.

Manfred Mutter, et al., "New Method of Polypeptide Synthesis," Angewandte Chemie, Int. Ed. Engl., 10:811–12 (1971).

Ernst Bayer, et al., "Synthese des Biologisch Aktiven Undecapeptids Substanz P nach der Flüssig–Phasen–Methode," Chem. Ber. 107:1344–52 (1974).

Peter Braun, et al., "Selective Enzymatic Removal of Protecting Functions: Heptyl Esters as Carboxy Protecting Groups in Peptide Synthesis," Synlett, Feb. 1990, pp. 105–107.

Peter Braun, et al., "Selektive Enzymatische Schutzqruppenabspaltungen: Der n–Heptylester als Carboxylschutzgruppe in der Peptidsynthese," Liebigs Ann. Chem. (1991) pp. 165–170.

Chemical Abstracts, vol. 95, 1981, pp. 734, No. 169102q.

Whitesides, et al. "Enzyme in der organischen Synthese," Angewandte Chemie, Jan. 1985, vol. 8, pp. 617–720.

Mutter et al., "The Liquid–Phase Method for Peptide Synthesis," The Peptides, vol. 2, 1979, Chapter 2, pp. 286–332.

Kunz et al., "Das System 2–Halogenethylester/Cholinester als Zweistufen–Schutgruppe fur die Carboxylfunktion von Aminosauren und Peptiden," Verlag Chemie, GmbH, 1979, pp. 2145–2156.

Buchholz et al., "Synthese von Glycopeptiden: Selektive c–terminale Deblockierung und Peptidkettenverlangerung an Glucosylserin–Derivaten," Liebigs Ann. Chem. 1983, pp. 1859–1885.

*Primary Examiner*—Cecilia J. Tsang
*Assistant Examiner*—Anish Gupta
*Attorney, Agent, or Firm*—Finnegan, Henderson, Farabow, Garrett & Dunner, L.L.P.

[57] ABSTRACT

Carboxylate protective groups, a process for their preparation, their coupling to a funcitonal group, and their use Carboxylates of polar, hydrophilic alcohols of the formula $$R'-C\overset{\displaystyle O}{\underset{\displaystyle O-R}{\diagup\!\!\!\!\diagdown}}$$

in which

R is an unbranched or branched organic radical which contains, as polar members between aliphatic or araliphatic hydrocarbon bridges, ether oxygens, amine nitrogen groups or a mixture of ether and amine groups which can be incorporated into a cyclic structure, where the total length does not exceed 20 members and where, in the case of polyethylene glycol $[(CH_2-CH_2-O)_n]$, n indicates the number of the members and is defined as any integer, and R' is an aliphatic or araliphatic radical which has at least one functional group, are suitable as protective groups since they can be introduced selectively into functional groups of organic compounds and eliminated specifically by lipases.

17 Claims, No Drawings

CARBOXYLATE PROTECTIVE GROUPS, A PROCESS FOR THEIR PREPARATION, THEIR COUPLING TO A FUNCTIONAL GROUP, AND THEIR USE

This is a division of application Ser. No. 08/226,367, filed Apr. 12, 1994, now U.S. Pat. No. 5,439,806, which was a continuation of application Ser. No. 07/957,004, filed Oct. 6, 1992, now abandoned.

The invention relates to carboxylates of polar, hydrophilic alcohols which are coupled to organic compounds for the protection of functional groups, to a process for the synthesis of the protective group, to a process for coupling the protective group to the functional group of an organic compound and to the elimination of the protective group from the organic compound by lipases.

A protective group is understood as meaning an organic radical by means of which functional groups of a molecule which contains a plurality of active centers can be protected temporarily against attack by reagents, so that reactions can only take place in the desired (unprotected) positions. When the reaction has ended, it should be possible to eliminate the protective group selectively (Römpps Chemielexikon, Franckh Fachlexikonverlag, Stuttgart, Germany, Volume 5, p. 3744–3745).

Lipases are ester hydrolases which, as is known, hydrolyze esters of fatty acids with glycerol or other alcohols and esters of carboxylic acids with fatty alcohols [G. M. Whitesides, C. H. Wong, Angew. Chem. 97 (1985), 617].

Lipases are employed successfully inter alia for removing protective groups from peptides. For example, amino acid and peptide n-heptyl (hep) esters which are prepared from unpolar alcohols can be cleaved enzymatically. These esters are the natural substrate of the lipases. (P. Braun, H. Waldmann, W. Vogt, H. Kunz, Syntlett 1990, 105). However, it has emerged that the enzymatic clearability depends highly on the structure. Extremely hydrophobic peptide esters such as, for example, Boc-Val-Phe-OHep, are not attacked by the previously known lipases on principle.

Japanese Patent 119,260 describes that carboxylates of hydrophilic alcohols are recognized by amidoacylases. However, the carboxylic acid derivative formed by the enzymatic cleavage is not used as a protective group but reacted with a further reactant to give the amide.

C.A. 95 (19) 1691902g likewise describes the above-described enzymatic cleavage, but instead of the free enzyme amidoacylase the entire microorganism Bacillus circulans M-1123-5, which also has amidoacylase activity, is employed.

Surprisingly, it has now been found that carboxylates of polar hydrophilic alcohols are suitable as protective group since they can be introduced selectively into functional groups of organic compounds and are eliminable specifically by lipases.

The invention relates to a compound of the formula I

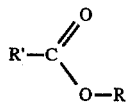

I in which

R is an unbranched or branched organic radical which contains, as polar members between aliphatic or araliphatic hydrocarbon bridges, ether oxygens, amine nitrogen groups or a mixture of ether and amine groups which can be incorporated into a cyclic structure, where the total length does not exceed 20 members and where, in the case of polyethylene glycol $[(CH_2-CH_2-O)_n]$, n indicates the number of the members and is defined as any integer, and R' is an aliphatic or araliphatic radical which has at least one functional group.

A process for the preparation of a compound of the formula I which comprises reacting a carboxylic acid of the formula R'—COOH, in which R' has one of the abovementioned meanings, with alcohols of the formula R—OH, in which R has one of the above-mentioned meanings, by esterification to give esters and reacting the resulting carboxylate of the hydrophilic, polar alcohol under the conditions of azeotropic esterification with the functional group of an organic compound.

The use of the carboxylate as a protective group, prepared from a polar hydrophilic alcohol, it being possible for the protective group to be eliminated by lipases.

The invention will be described in detail hereinafter. It is furthermore described by the contents of the claims.

Organic hydrocarbon compounds which are defined as araliphatic contain both aromatic and aliphatic radicals.

The protective groups are prepared from polar, hydrophilic alcohols and any desired carboxylic acids by processes known to a person skilled in the art.

The protective groups according to the invention have a very broad spectrum of application. They can be coupled with molecules of organic compounds which have functional groups on a plurality of active centers.

Functional groups are defined as hydroxyl, thiol, amino, carbonyl or carboxyl groups which can exist in protected and/or unprotected form.

The abovementioned molecules are, in particular, amino acids, peptides, glycopeptides, carbohydrates or their esters with diethylene glycol monomethyl ether (Dem) of the structure 1, with 2-(morpholino)ethyl ester (MoEt) of the structure 2 and with PEG (polyethylene glycol) of the structure 3.

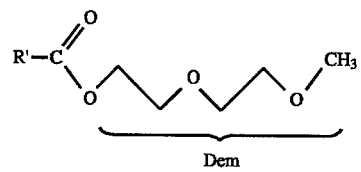

Dem

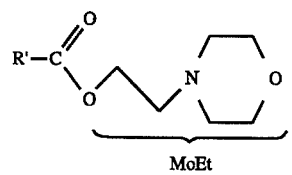

MoEt

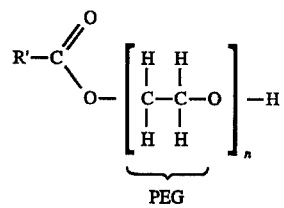

PEG

Apart from the protected functional group, the molecules have at least one further functional group, where the reaction sensibly takes place. If there are two or more functional groups within one molecule, other protective groups can be introduced in addition to the above-mentioned one. To this end, identical or different protective groups can be used.

The size of the peptides is preferably 1–100 amino acids, but in particular 1–50 amino acids and very preferably 1–25 amino acids.

The compounds of the formula I are preferably employed as protective group when R'—C=O is a protected or unprotected amino acid radical or peptide acyl radical.

It is a particular property of the compounds of the formula I that the alcoholic moiety R has polar, hydrophilic properties as caused, for example, by oligo- and polyether structures of the ethylene glycol ester type or by amine and ether groups in the chain. If the acyl radical R' has hydrophobic character, the compounds of the formula I still have sufficiently great solubility in water or in water-containing solvents. This applies in particular to amino acid esters and peptide esters which are protected N-terminally and in the side chains and whose carboxyl groups are protected in the above-described ester form.

Coupling of the protective groups according to the invention with the reactants is also effected by processes known to a person skilled in the art. For example, amino acids are reacted with diethylene glycol monoethyl ether under the conditions of azeotropic esterification. The reaction can also be effected by the process of Kunz and Buchholz (Chem. Ber. 112 (1979, 2145) or analogously to the process of Buchholz and Kunz (Liebigs. Ann. Chem. 1983, 1859). These two processes are preferably employed in the case of MoEt. Coupling can furthermore be effected by the process developed by Mutter and Bayer (M. Mutter and E. Bayer in "The Peptides" Academic Press, New York 1979, Chapter 2, p. 286–329), preferably in the case of polyethylene glycol.

As already mentioned above, lipases eliminate the protective groups specifically. All commercially available lipases can be used for this purpose.

Before the enzymatic cleavage is started, it is necessary to test the lipase for contamination with proteases. Proteases must be blocked by phenylmethylsulfonyl fluoride (PMSF) using methods known to a person skilled in the art.

Enzymatic elimination of the polar, hydrophilic carboxyl protective groups by lipases is effected by methods known to a person skilled in the art in aqueous media, preferably 90% of water and 10% of acetone (v/v) at a pH of 7.0. The reaction time is 12–48 hours at 37° C.

EXAMPLE 1

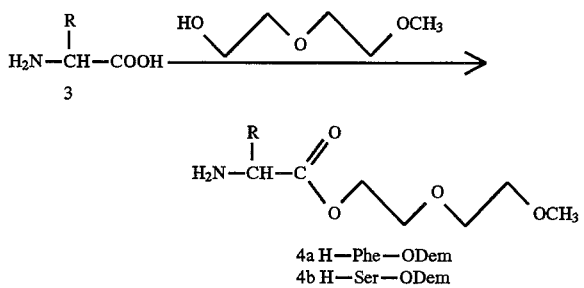

4a H—Phe—ODem
4b H—Ser—ODem

The 2-(morpholino)ethyl esters are expediently prepared from the 2-bromoethyl esters of the amino acid or of the peptides and glycopeptides, prepared by the protocol of H. Kunz, M. Buchholz, Chem. Ber. 112 (1979), 2145, or obtained analogously to the process of M. Buchholz, H. Kunz, Liebigs. Ann. Chem. 1983, 1859, by reaction with morpholine (see Examples 2 and 3).

EXAMPLE 2a

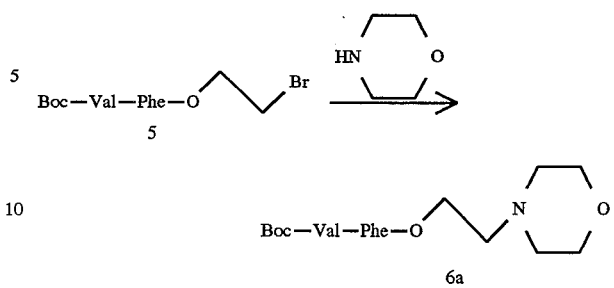

EXAMPLE 3

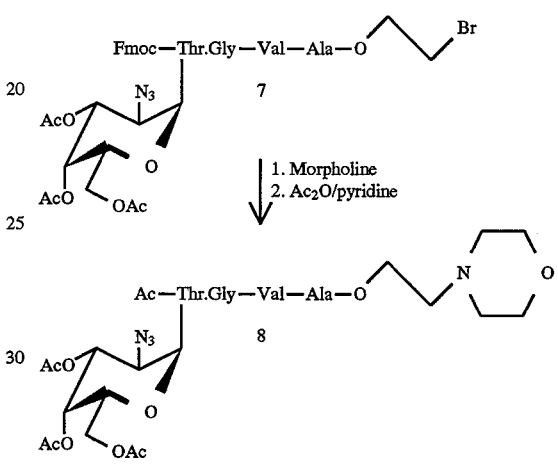

The amino acid esters obtained are linked with N-protected amino acids or peptides to give higher peptide units.

EXAMPLE 4

EXAMPLE 4a

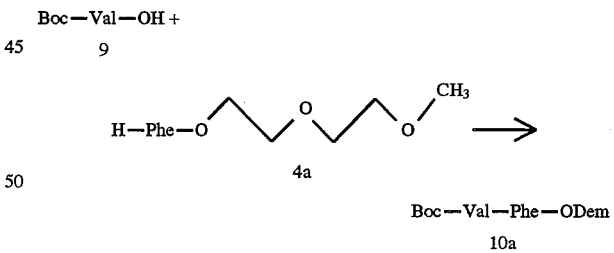

Boc—Val—Phe—ODem

10a

The polar, hydrophilic carboxyl protective groups are eliminated from the resulting peptides and glycopeptides, which are protected C-terminally according to the invention, by means of lipases (see Example 5a–h) in aqueous media (as a rule, water and 10% v/v acetone) at pH 7 in the course of 12 h to 48 h (in the case of complex glycopeptides such as 8). Since the conditions are neutral and exceptionally mild (37° C.), all other protective groups on the peptides and glycopeptides, some of which are very complex, are retained. This applies to the base-labile Fmoc groups, to the Z and trichloroethoxycarbonyl (Teoc) groups, which can be removed by means of reduction, and to acid-labile groups, for example the Boc group.

EXAMPLES 5a–h:

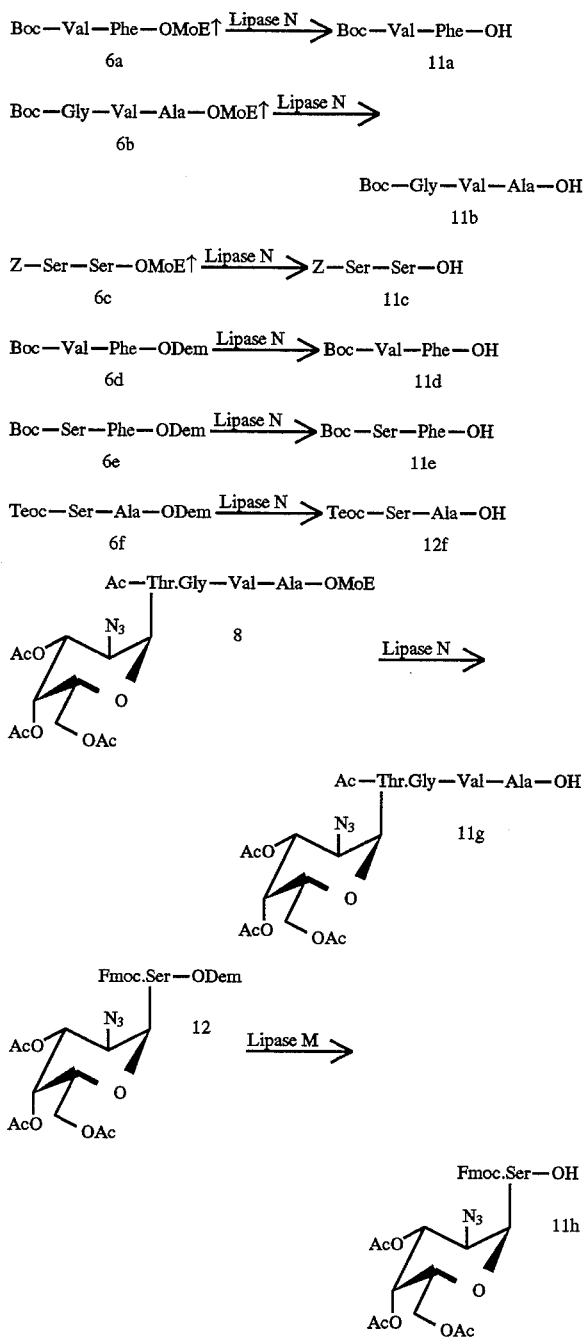

The proteases frequently found in lipase preparations must be blocked carefully by adding phenylmethylsulfonyl fluoride (PMSF). The results of the enzymatic elimination of protective groups demonstrate that the esters according to the invention, in this case having a diethylene glycol and 2-(morpholino)ethyl structure, are accepted by the lipase as substrates and hydrolyzed despite their polar, hydrophilic character. Even those peptide sequences such as the hydrophobic compounds 6 and 10a, whose heptyl esters were not attacked, are hydrolyzed without difficulty. It can be concluded that the polar esters which can be cleaved by lipases can be removed enzymatically not only on fat-like but also on polar carboxyl components.

EXAMPLES 6 and 6a

Synthesis of esters according to the invention of structure 1
General protocol for the preparation of amino acid esters with diethylene glycol monomethyl ether 4

A mixture of 0.15 mol of amino acid 3, 0.8 mol of diethylene glycol monomethyl ether, 0.18 mol of p-toluenesulfonic acid hydrate and 150 ml of benzene is refluxed with elimination of water until water is no longer eliminated (24 h). When the reaction has ended, the benzene is distilled off under a waterpump vacuum, and the excess diethylene glycol monomethyl ether is then distilled off under a high vacuum. For purification, the residue is digested several times in ether and subsequently dried under a high vacuum. Compounds 4a and 4b are reacted to give the protected dipeptides 10a and 10b, and these are characterized analytically.

a) L-phenylalanine [diethylene glycol (monomethyl ether) ester] hydro-p-toluenesulfonate 4a
b) L-serine [diethylene glycol (monomethyl ether) ester] hydro-p-toluenesulfonate 4b

EXAMPLES 7a–c

Synthesis of esters according to the invention of structure 2
General protocol for the preparation of 2-morpholinoethyl esters from bromo- and iodoethyl esters A solution of 5 mmol of 2-haloethyl ester in 15 ml of morpholine is stirred at 25° C. for 1–4 hours. The morpholine is subsequently distilled off in vacuo, the residue which remains is taken up in ether, and the mixture is extracted by shaking with ice-cold 0.5N hydrochloric acid. The combined aqueous phases are brought to pH 9 using sodium hydrogen carbonate and extracted using methylene chloride. For purification, the morpholinoethyl ester which is protected according to the invention is first dried over magnesium sulfate, the solvent is distilled off in vacuo, and the ester is then brought to crystallization using a small amount of ether.

a) N-tert-butyloxycarbonyl-L-valyl-L-phenylalanine 2-morpholinoethyl ester 6a
Yield: 95%, m.p.: 83°–84° C. $[\alpha]_D^{22}$=15.6 (c=1; CHCl$_3$).
b) N-tert-butyloxycarbonyl-glycyl-L-valyl-L-alanine 2-morpholinoethyl ester 6b
Yield: 64%, m.p.: 115°–116° C., $[\alpha]_D^{22}$=0.9 (c=1.1; CHCl$_3$).

EXAMPLE 8

Synthesis of a glycopeptide ester according to the invention of the structure 2
N-Acetyl-3-O-(3,4,6-tri-O-acetyl-2-azido-2-deoxy-α-D-galactopyranosyl)-L-threonyl-glycyl-L-valyl-L-alanine 2-morpholinoethyl ester 8 is prepared by a variant of the general protocol in Example 2:

1.5 g (1.5 mmol) of N-(9-fluorenylmethoxycarbonyl)-3-O-(3,4,6-tri-O-acetyl-2-azido-2-deoxy-β-D-galactopyranosyl)-L-threonyl-glycyl-L-valyl-L-alanine 2-bromoethyl ester 7 is stirred for 30 minutes at room temperature in 5 ml of freshly distilled morpholine. The reaction mixture is concentrated in vacuo at a bath temperature of not more than 40° C. and codistilled several times using toluene and ether until all of the morpholine has been removed. The residue is treated with 10 ml of a cooled mixture of acetic anhydride/pyridine (2:1) and stirred for 2 hours at 20° C. The reaction mixture is subsequently concentrated in vacuo and codistilled several times using toluene. The resulting residue is dissolved in 50 ml of methylene chloride, and the solution is extracted several times using ice-cold 0.5N hydrochloric acid. The collected aqueous phases are adjusted to pH 8.5 using sodium hydrogen carbonate and extracted by shaking with methylene chloride. The combined organic phases are washed with 20 ml of saturated sodium chloride solution, dried over magnesium sulfate and concentrated in vacuo. The residue is purified on 80 g of silica gel 60 (manufactured by Merck, Darmstadt, Germany) by flash chromatography (mobile phase $CH_2Cl_2/EtOH$, 10:1).

Yield: 0.53 g (0.65 mmol); 43% $[\alpha]_D^{22}$=54.4 (c=1; $CHCl_3$).

EXAMPLES 9a–c

Synthesis of a peptide ester according to the invention of the structure 1

N-Protected dipeptide Dem ester 10 with the aid of 1-ethoxycarbonyl-2-ethoxy-1,2-dihydroquinoline (EEDQ, O)

To a solution of 0.01 mol of amino acid Dem ester hydro-p-toluenesulfonate 4 and 0.01 mol of diisopropylethylamine in 20 ml of dichloromethane there is added a solution of 0.01 mol of N-protected amino acid 9 in 20 ml of dichloromethane and 0.012 mol of EEDQ, and the mixture is stirred for 12 hours at room temperature. The reaction mixture is subsequently extracted three times in each case with 0.5N HCl, 0.5N $NaHCO_3$ and water, dried over magnesium sulfate and concentrated in vacuo. The crude product is purified by flash chromatography (petroleum ether/ethyl acetate).

a) N-tert-butyloxycarbonyl-L-valyl-L-phenylalanine Dem ester (10a)

Yield: 71%, waxy substance, $[\alpha]_D^{22}$=23.3 (c=0.9; $CHCl_3$).

b) N-tert-butyloxycarbonyl-L-seryl-L-phenylalanine Dem ester (10b)

Yield: 64%, waxy substance, $[\alpha]_D^{22}$=−6.6 (c=1.0; $CHCl_3$).

c) N-trichloroethyloxycarbonyl-L-alanyl-L-serine Dem ester (10c)

Yield: 74%, oil, $[\alpha]_D^{22}$=−3.4 (c=1.1; $CHCl_3$).

EXAMPLE 10a–h

Enzymatic cleavage of the esters according to the invention of structure 1 or 2

General protocol for the enzymatic elimination of the protected esters according to the invention. 1. Inhibition of protease activity of the enzyme preparation:

200 mg of Lipase N (manufactured by Amano) are dissolved in 1 ml of 0.2M phosphate buffer (pH 7), 3.5 mg of phenylmethylsulfonyl fluoride (PMSF) are added, and the mixture is stirred for 1 hour at 0° C. and for 1 hour at 37° C.

2. C-terminal deblocking:

The enzyme solution is made up to 25 ml with phosphate buffer and stirred for 16 hours at 37° C. together with a solution of 200 mg of ester protected according to the invention in not more than 2.5 ml of acetone. The reaction solution, which has been brought to a pH of 8.5 using sodium hydrogen carbonate, is then diluted with 10 ml of water and extracted with ether. The water phase, which has been adjusted to pH 4 using potassium hydrogen sulfate, is extracted by shaking with ethyl acetate. The combined ethyl acetate phases are dried over magnesium sulfate and concentrated in vacuo. If necessary, the carboxyl-deblocked product can be purified by flash chromatography using an ethyl acetate/ethanol mixture. For example, the following compounds are obtained from the corresponding 2-morpholinoethyl esters:

a) N-tert-butyloxycarbonyl-L-valyl-L-phenylalanine 11a
Yield: 91%, amorphous, $[\alpha]_D^{22}$=14.2 (c=1.0; $CHCl_3$).

b) N-tert-butyloxycarbonyl-glycyl-L-valyl-L-alanine 11b
Yield: 78%, m.p.: 179° C., $[\alpha]_D^{22}$=−31.9 (c=1.0; $CH_3OH$).

c) N-benzyloxycarbonyl-L-seryl-serine 11c
Yield: 78%, amorphous, $[\alpha]_D^{22}$=12.1 (c=0.6; $CH_3OH$).

The compounds 11d–f are obtained from the corresponding diethylene glycol monomethyl esters:

The dipeptide acids 11d–f, which are obtained by enzymatic hydrolysis of the Dem esters, are characterized as dicyclohexylamine (DCHA) salts.

d) N-tert-butyloxycarbonyl-L-valyl-L-phenylalanine*DCHA 11d
Yield: 97%, amorphous, $[\alpha]_D^{22}$=−14.3 (c=1.0; $CH_3OH$).

e) N-tert-butyloxycarbonyl-seryl-L-phenylalanine*DCHA 11e
Yield: 94%, m.p.: 184° C., $[\alpha]_D^{22}$=15.4 (c=1.0; $CH_3OH$).

f) N-trichloroethyloxycarbonyl-L-alanyl-L-serine*DCHA 11f
Yield: 92%, m.p.: 172°–175° C., $[\alpha]_D^{22}$=−1.0 (c=0.65; $CH_3OH$).

To cleave the ester groups according to the invention on glycopeptides, an enzyme solution is prepared from 400 mg of lipase which, after a reaction time of no more than 48 hours, is saturated with sodium chloride and extracted using ethyl acetate. The ethyl acetate phase, which has been dried over magnesium sulfate, is concentrated in vacuo, and the resulting residue is purified by chromatography on silica gel.

The following are obtained from the corresponding 2-morpholinoethyl ester 8:

g) N-acetyl-3-O-(3,4,6-tri-O-acetyl-2-azido-2-deoxy-α-D-galactopyranosyl)-L-threonyl-glycyl-L-valyl-L-alanine 11g
Yield: 59%; amorphous solid, $[\alpha]_D^{22}$=56.2 (c=0.54; MeOH).

The corresponding diethylene glycol monomethyl ester 12 gives the glycopeptide 11h, Lipase M (manufactured by Amano) being used for the enzymatic hydrolysis under the above-described experimental conditions.

h) N-(9-fluorenylmethoxycarbonyl)-3-O-(3,4,6-tri-O-acetyl-2-azido-2-deoxy-α-D-galactopyranosyl)-L-serine 11h
Yield: 64%, foam, $[\alpha]_D^{22}$=92.2 (c=1.1; $CH_3OH$).

EXAMPLE 11

Protocol for the synthesis of peptides on a polyethylene glycol matrix a) Protocol for the esterification of the C-terminal amino acid with polyethylene glycol:

Coupling is effected by a method described by M. Mutter and E. Bayer. 8 mmol of N-(9-fluorenylmethoxycarbonyl)-L-amino acid and 820 mg (mmol) of dicyclohexylcarbodiimide are stirred for 30 minutes at room temperature in 10 ml of methylene chloride. The anhydride formed is separated from the precipitated urea by filtration and a four-fold excess of the product is added to the polyethylene glycol (MW 6000) which has been dried in a high vacuum. The reaction solution Is treated with 1 ml of pyridine, concentrated and stirred at room temperature. After 6 hours, the mixture is evaporated to dryness in vacuo and the product is dissolved in 20 ml of methylene chloride. The polyethylene glycol ester is crystallized from this solution by an addition of approximately 150 ml of absolute ether, with stirring at −10° C. When the addition of ether has ended, stirring is continued at −10° C. for 10 minutes, and the product is filtered rapidly using a frit, washed several times with ether and dried over $P_2O_5$.

If incomplete esterification is to be expected, which is the case in particular with trifunctional amino acids, the unreacted OH groups are blocked with acetic anhydride/pyridine. Purification is effected by crystallization as described above.

General protocol for the N-terminal elimination of the Fmoc group and elongation by the carbodiimide method:

The polyethylene glycol ester is dissolved in the 10-fold amount of morpholine, and the solution is stirred for one hour at room temperature. The deblocked compound is purified by crystallization as described above and immediately elongated further. To this end, the N-terminally deblocked polyethylene glycol ester is reacted with 4 equivalents of N-(9-fluorenylmethoxycarbonyl)-L-amino acid, 6 equivalents of DCC and 8 equivalents of HOBt in methylene chloride/DMF. After the mixture has been stirred for 4 to 6 hours at 25° C., the urea which has precipitated is separated off, and the product is worked up as usual.

In this manner, the following peptides were synthesized:

N-(9-fluorenylmethoxycarbonyl)glycyl-L-valine PEG 6000 ester

N-(9-fluorenylmethoxycarbonyl)-L-valyl-L-alanine PEG6000 ester

N-(9-fluorenylmethoxycarbonyl)-L-prolyl-L-alanine PEG 6000 ester

The enzymatic cleavage is carried out following the general protocol mentioned in German Patent Application P41 33 139.7. To calculate the yields, it is assumed that all coupling steps were quantitative. Using $^1H$ 200 MHz NMR spectroscopy, it was possible to detect unequivocally in each case the successful elimination of the polyethylene glycol and the correctness of the peptide structure.

N-(9-fluorenylmethoxycarbonyl)glycyl-L-valine

Yield: 90%, m.p.: 69°–71° C., $[\alpha]_D^{22}$=−0.5 (c=1.0; $CH_3OH$).

N-(9-fluorenylmethoxycarbonyl)-L-valyl-L-alanine

Yield: 66%, m.p.: 122°–123° C., $[\alpha]_D^{22}$=−44.3 (c=1.1; $CH_3OH$).

N-(9-fluorenylmethoxycarbonyl)-L-prolyl-L-prolyl-L-alanine

Yield: 50%, m.p.: amorphous, $[\alpha]_D^{22}$=−72.5 (c=1.0; $CH_3OH$).

FAB-MS (negative ion detection): m/z=505 (M-1) Matrix: glycerol

EXAMPLE 12

Protocol for the preparation of the diethylene glycol (monomethyl ether) ester of cholic acid A mixture of 0.01 mol of cholic acid, 0.1 mol of diethylene glycol monomethyl ether, 0.1 mmol of p-toluenesulfonic acid hydrate and 30 ml of benzene is refluxed with elimination of water until water is no longer eliminated (72 h). When the reaction has ended, the benzene is distilled off under a waterpump vacuum, and the excess diethylene glycol monomethyl ether is then distilled off under a high vacuum. For working up, the residue is taken up in 50 ml of ethyl acetate and extracted using a saturated sodium carbonate solution. The organic phase is dried using magnesium sulfate and concentrated. For purification, the residue is reprecipitated from ethyl acetate/petroleum ether.

Yield: 23% (colorless white crystals), m.p.: 102°–105° C., $[\alpha]_D^{22}$: 21.6 (c=1.1, $CH_3OH$)

EXAMPLE 13

Protocol for the enzymatic hydrolysis of cholic acid DEM ester by means of porcine liver esterase (PLE; Amano)

0.5 mmol of cholic acid Dem ester are suspended in a solution of 250 mg of PLE (Amano) in 250 ml of 0.2M sodium phosphate buffer (pH 7), and the suspension is shaken for 72 hours at 37° C. For working-up, the mixture is saturated with sodium chloride and extracted using ethyl acetate. The combined organic phases are dried over magnesium sulfate, the solvent is distilled off in vacuo, and the residue is purified by means of flash chromatography (PE/EA).

Yield: 69% (colorless white crystals); m.p.: 195°–197° C.; $[\alpha]_D^{22}$: 33 (c=0.6, ethanol).

The $^1H$ 200 MHz NMR spectrum agrees with that of commercially available cholic acid.

We claim:

1. A process for peptide synthesis comprising esterifying a functional group selected from an amino acid, a peptide, or a glycopeptide, whose N-terminal amino group is protected or unprotected and optionally having attached to said functional group additional functional groups in protected or unprotected form, to form a compound of formula I:

which is protected at the carboxyl end and in which R is an unbranched or branched organic radical which contains an ether oxygen, an amine nitrogen group, or a mixture of ether and amine groups as polar members between aliphatic or araliphatic hydrocarbon bridges optionally incorporated in a ring structure whose overall length does not exceed 20 members, and in the case of polyethylene glycol of the formula ($CH_2$—$CH_2$—O)$_n$, where n represents the number of members and is any integer, and

is an amino acid radical, a peptide radical, or a glycopeptide radical, and eliminating the R radical at the carboxyl end by means of a lipase dissolved in water or in an aqueous solution, with enzymatic catalysis.

2. The process as claimed in claim 1, wherein the hydrocarbon bridges between the polar members in the radical R are ethylene members of the structure, —$CH_2$—$CH_2$—.

3. The process as claimed in claim 2, wherein the polar members between the ethylene bridges in the radical R are oxygen.

4. The process as claimed in claim 2, wherein the polar members between the ethylene bridges in the radical R are nitrogen functions of the structure N—$R^2$ wherein $R^2$ is H or lower alkyl, and wherein the polar members are optionally linked with the ethylene bridges to form a ring.

5. The process as claimed in claim 1, wherein the polar members in the radical R are both oxygen and amine nitrogen functions.

6. The process as claimed in claim 1, wherein the group R'—CO is a peptide radical composed of 1 to 100 amino acids.

7. The process as claimed in claim 6, wherein the peptide radical is composed of 1 to 50 amino acids.

8. The process as claimed in claim 7, wherein the peptide radical is composed of 1 to 25 amino acids.

9. The process as claimed in claim 1, wherein the group R'—CO is a glycopeptide radical.

10. The process as claimed in claim 1, wherein R in formula I is a diethylene glycol monomethyl ether radical (DEM).

11. The process as claimed in claim 10, wherein a compound of the formula R'—COOH in which R'CO is an amino acid radical, a peptide radical, or a glycopeptide radical reacts with an alcohol of the formula R—OH in which R has the meaning given in claim 10 under the conditions of azeotropic esterification to form a compound of formula I.

12. The process as claimed in claim 1, wherein R in the compound of the formula I is a 2-(morpholino)ethyl group.

13. The process as claimed in claim 1, wherein R in the compound of the formula I is a polyethyelene glycol (PEG) group.

14. The process as claimed in claim 12, wherein a haloalkyl ester of the formula R'—COO—$CH_2$—$CH_2$—X in which X is Cl, Br, or I, is reacted with morpholine to form the 2-(morpholino)ethyl ester.

15. The process as claimed in claim 1, wherein the enzymatic hydrolysis is effected by catalysis with a lipase dissolved in water or an aqueous solution in the presence of complexing ions.

16. The process as claimed in claim 15, wherein said complexing ions are alkali metal ions.

17. The process as claimed in claim 1, further comprising, prior to eliminating the R radical, deprotecting the N-terminal amino group of the compound of formula I and linking said compound of formula I with N-protected amino acid to give a higher peptide unit.

* * * * *